United States Patent [19]

Wilson et al.

[11] 4,345,463

[45] Aug. 24, 1982

[54] ON-LINE GAS MEASUREMENT AND ANALYSIS SYSTEM

[75] Inventors: Wayne Wilson, Houston, Tex.; George Rosko, Toms River; James R. Patmore, Neptune, both of N.J.

[73] Assignee: Electronic Associates, Inc., West Long Branch, N.J.

[21] Appl. No.: 142,670

[22] Filed: Apr. 22, 1980

[51] Int. Cl.$^3$ .................... G01N 31/06; G01K 17/06
[52] U.S. Cl. ................................ 73/190 CV; 73/23.1
[58] Field of Search ............. 73/23.1, 190 R, 190 CV; 364/509, 510, 465

[56] References Cited

U.S. PATENT DOCUMENTS 3,095,728  7/1963  Kindred et al. .................... 73/23.1
3,752,393  8/1973  Moseley ............................ 364/510

FOREIGN PATENT DOCUMENTS 2528443  1/1977  Fed. Rep. of Germany ........ 73/190 CV

OTHER PUBLICATIONS

Agar, J. "The Use of a Density Meter and Microprocessor for Energy Measurement and Control", Appalachian Gas Measurement Short Course, 1978.
Jenkins, D. L. and Robinson, K. "Densitometers for Energy Measurement", Appalachian Gas Measurement Short Course, 1978.
Howard, R. L. "Determination of Calorific Value of Natural Gases", Fifty Third International School of Hydrocarbon Measurement, 1978.
Scholtes, D. F. "Maintenance and Operation of the Electronic Calorimeter", Fifty Third International School of Hydrocarbon Measurement, 1978.
Chambers, T. L. "From MCF to MMBTU", Fifty Third International School of Hydrocarbon Measurement, 1978.
Schwartz, R. D. "Gas Chromatography", Fifty Third International School of Hydrocarbon Measurement, 1978.

*Primary Examiner*—James J. Gill
*Attorney, Agent, or Firm*—Ratner & Prestia

[57] ABSTRACT

A system for measuring on-line the energy content and flow of a gas mixture within a pipeline. The system includes a gas chromatograph for producing a time varying signal related to the component composition of the gas mixture. The pressure and temperature of the gas mixture is measured and these signals as well as the time varying signal from the chromatograph are converted to digital form. These signals are applied to control means which produces energy and flow rate signals of the gas mixture in the pipeline based on the on-line pressure, temperature and component composition. These signals are corrected by supercompressibility factor signals as a function of component composition.

14 Claims, 6 Drawing Figures

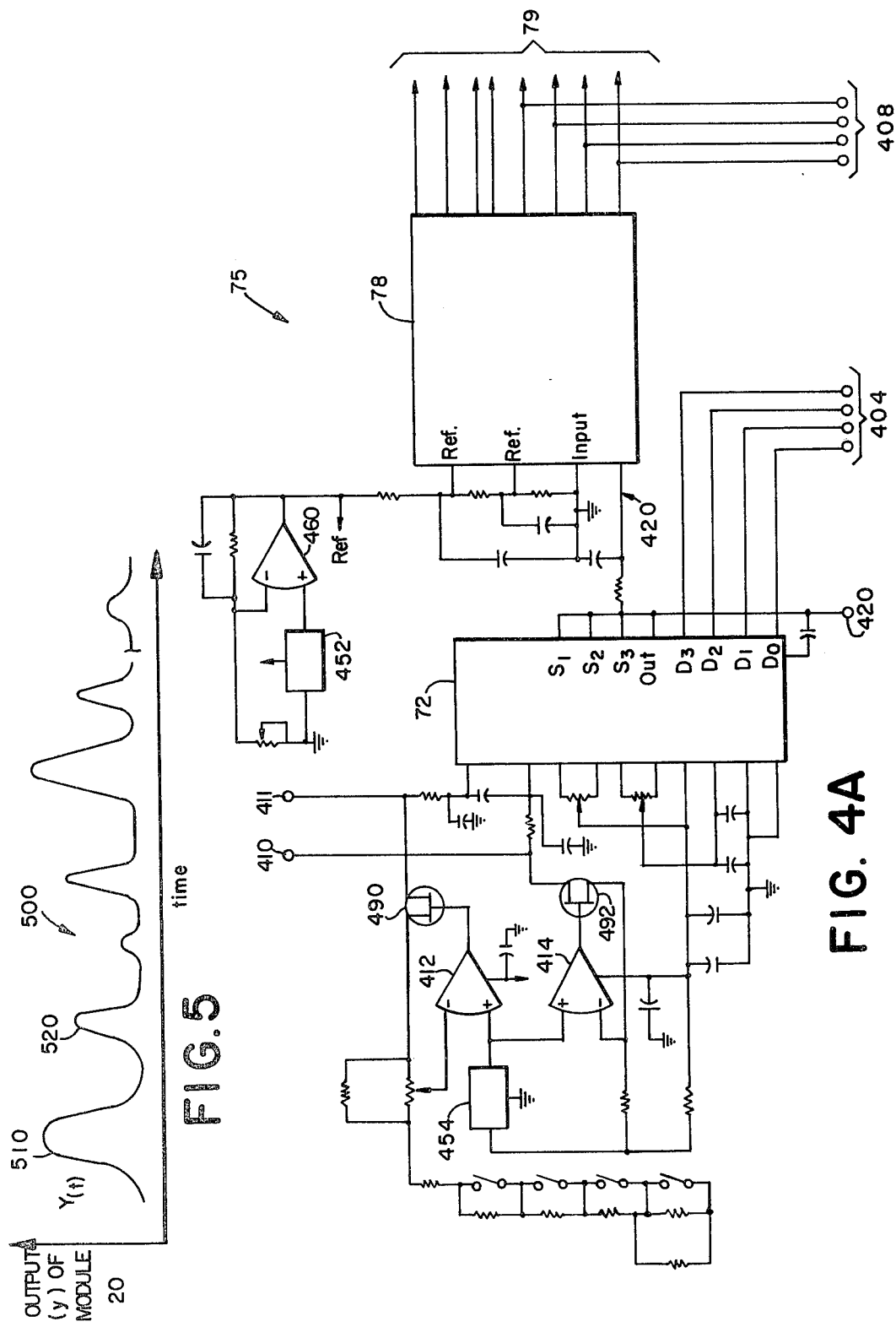

ON-LINE GAS MEASUREMENT AND ANALYSIS SYSTEM

BACKGROUND OF THE INVENTION

A. Field of the Invention

This invention relates to the field of art of on-line gas measurement and analysis systems and particularly with respect to gas chromatograph systems.

B. Background Art

It has become increasingly important, particularly over the last several years, to quantitatively measure the amount of natural gas being transmitted through a pipeline. This requirement has been based on the heating value or calorific content of the natural gas traveling through the pipeline when it has been sold or otherwise transferred. All of those involved in the sale, purchase and transmission of the natural gas now recognize the need for the highest possible accuracy in both energy content and flow measurement.

In the past some approaches to energy measurement have been taken, generally based on indirect measurement techniques with energy content manually integrated with flow data. Such indirect measurement generally consisted of estimates and assumptions of many physical parameters found in both flow and energy equations. Each of these techniques has relied on assumptions that a given operating parameter or set of parameters remains constant over some period i.e. pressure, temperature, supercompressibility and others. By definition, each of these assumptions introduces inaccuracies in energy measurement. Economic pressures result from the rapid escalation of the cost of fuel gas. As the cost of gas increases, the marginal cost increases. Specifically, present methods of measurement permit too great a margin of error, as the cost of the fuel unaccounted for becomes significant due to the price increases per unit of fuel. In this same light, both purchasers and suppliers of fuel gas have been utilizing contracts which specify a price per "Dekatherm", a unit of energy content, rather than simply cost per volume, (dollars per cubic feet, for example). Economic pressure and increased use of "Dekatherm" contracts have combined to dictate the use of more accurate total energy measurement for fuel gas.

SUMMARY OF THE INVENTION

A system for measuring on-line the total energy and total fluid flow of a gas mixture within a pipeline having a gas chromatograph for producing time varying signals related to the component compositions within the pipeline. The time varying signal is converted to digital form. Transducer means measure the pressure and temperature of the gas mixture and provides signals thereof in digital form. Control means is connected to the transducer means and to the converting means for producing energy and flow rate signals of the gas mixture in the pipeline based on the on-line pressure, temperature and component gas composition.

Further in accordance with the invention there is provided programmable gain means coupled to the gas chromatograph and having a plurality of gain ranges. Comparative means selects a gain range for optimum resolution and produces a related gain range signal which is applied to the control means.

BRIEF DESCRIPTION OF THE DRAWINGS

FIGS. 4A, 4B taken together show an electronic schematic diagram of the gas chromatograph interface portion of FIG. 1; and FIG. 5 is a graphic representation of the output of the gas chromatograph of FIG. 1.

GENERAL DESCRIPTION

Figure 1:
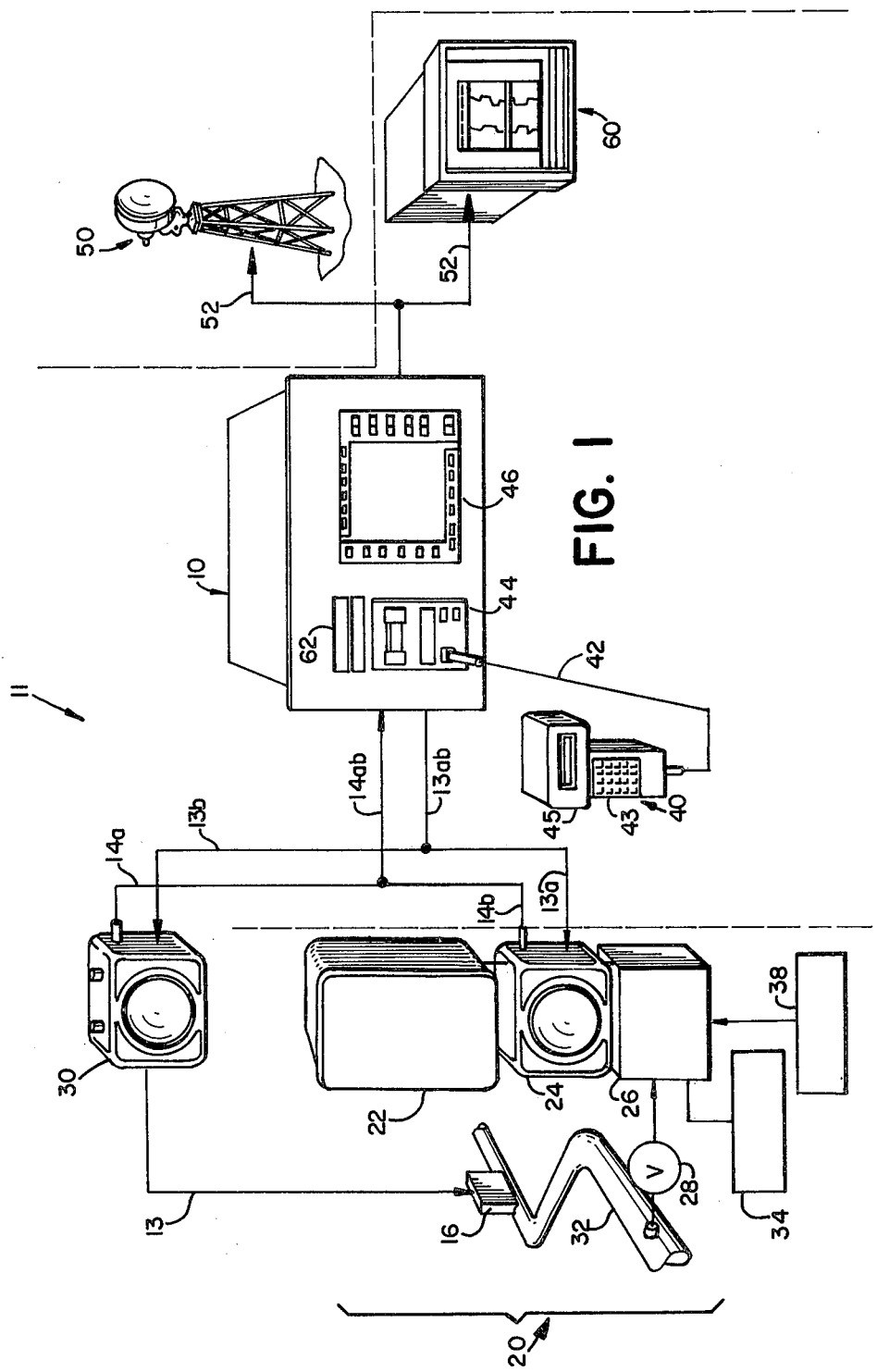
FIG. 1 is a pictorial diagram of the entire energy measurement system of the present invention.

The total energy measurement system shown in FIG. 1 provides both total accumulated energy and total flow rate and total energy rate as primary outputs, with respect to a given point in a fuel gas pipeline. Secondary informational outputs include real specific gravity, gas composition, and both flow and energy rates. With respect to gas pipelines, orifice metering of flowing gas is a well accepted, proven measurement technique. However, the measurement of volume flow is no longer sufficient to many users and total energy measurement is necessary.

The total energy measurement system 11 may be divided into sections as follows: a flow measurement section using American Gas Association measurement report No. 3 orifice metering techniques (this section consisting of a flow transducer module 16 and a transducer interface module 30); a process chromatograph providing compositional data on the flowing fuel gas (the remote analyzer module 20); and a microcomputer for system control and computational capability (basic control module 10).

The flow transducer module includes all those devices in common use for orifice flow measurement-meter tubes, orifice fittings, plates, static and differential pressure transmitter and a common flowing temperature transmitter. Through the use of a microprocessor, up to six meter tubes may be serviced simultaneously. Servicing not only includes the capability to convert signals from the transducer, but also the ability to bring meter tubes automatically in or out of service as the demand dictates. This is accomplished through use of operator-input minimum and maximum differentials permitted across the orifices.

The remote analyzer module contains a gas chromatograph subsystem which is an analytical device, and under control of the microcomputer in the basic control module, provides compositional analysis on a sample of a flowing gas. The analog voltage level output of the gas chromatograph subsystem is converted to digital signals and transmitted to the microcomputer in the basic control module. Each peak in the voltage output, (over time), of the chromatograph represents one component of the gas. The time at which the apex of each voltage peak occurs serves to identify the component. The area of each peak is proportional to the concentration of that component of a mixture. (See Rosko and Hass, "New Total Energy Measurement System Developed", PIPELINE AND GAS JOURNAL, August, 1979.)

Analysis of gases with the energy measurement system takes approximately 10 minutes to complete. Thus, new compositional data on the gas may be obtained every 10 minutes.

The total energy measurement system, described in detail provides the following information: gas compositional analysis; gross dry or gross wet BTU/SCf; real specific gravity; flow rate (ft$^3$/hr.); energy rate (dekatherms/hr) and total flow (ft$^3$), both continuous, hourly and daily; and total energy both continuous, hourly and daily. The entire process in the system utilizes measured variables and no assumed values are used in any calculation which are performed.

DETAILED DESCRIPTION

The invention will now be described in more detail with reference to the various figures. The description will be regemented into several areas for discussion, including the remote analyzer module 20, transducer interface module 30, and the basic control module 10.

Figure 2:
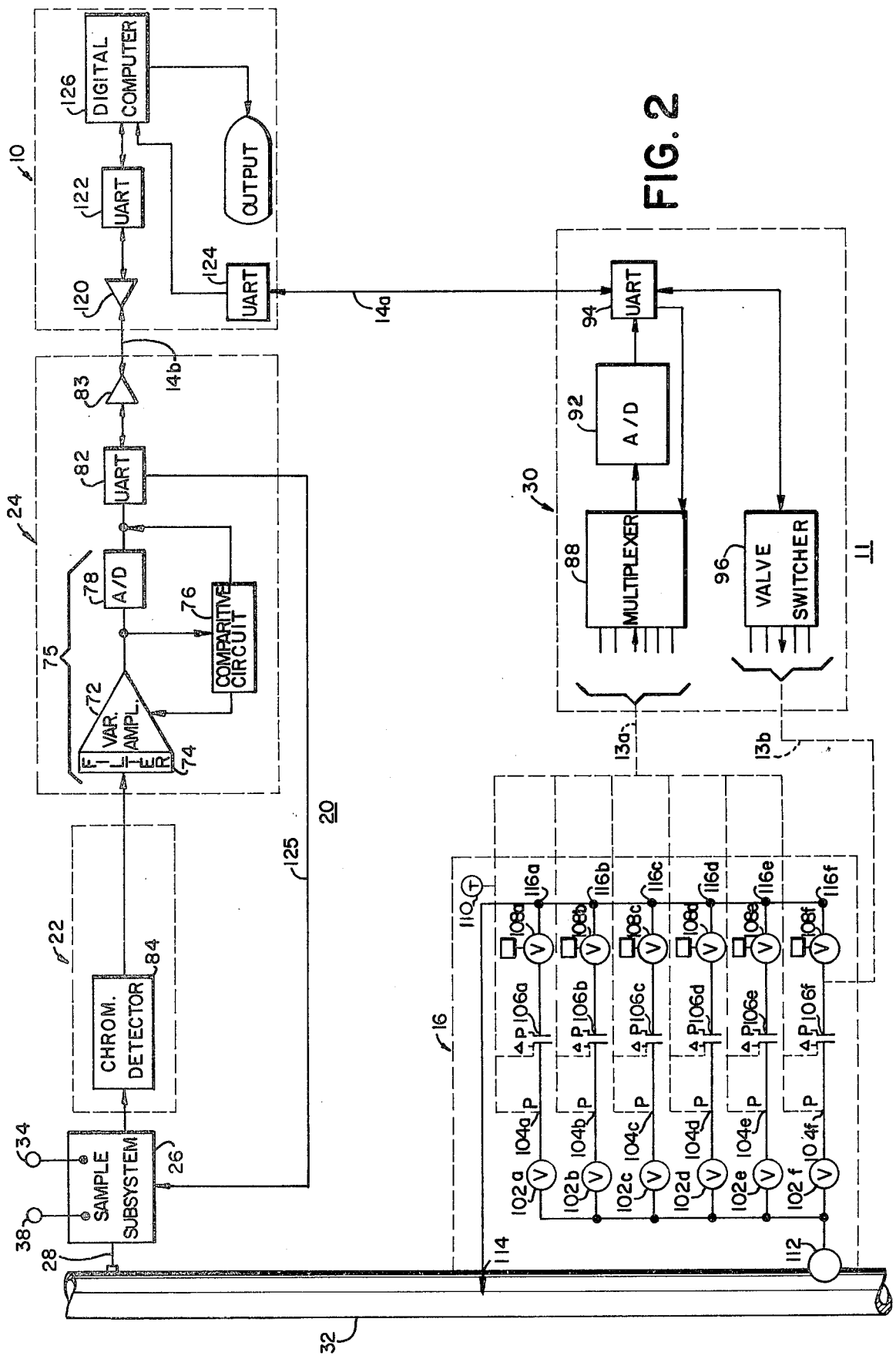
FIG. 2 is a block diagram of the energy measurement system of FIG. 1.

Turning now to the remote analyzer module 20, shown in FIG. 1 and detailed in FIG. 2, this module includes the chromatograph subsystem 22, the interface subsystem 24, and the sample manifold subsystem 26. The sample tap 28, provides a sample of the gas in the pipeline 32 to the sample manifold system 26. Attached to the sample manifold 26 are gas canisters of both a calibration gas mixture 34 and a carrier gas 38, usually helium. The calibrated gas mixture 34, is used to compare its known qualities with the unknown qualities of the sampled gas. The carrier gas 38 is utilized as a neutral transportation agent which facilitates the processing of both the sampled gas and the calibration mixture. It accomplishes this by providing pressurization, where necessary, so as to allow a small quantity of fuel gas from the pipeline 32 or the calibrated gas mixture 34 to be transported from the sampling subsystem 26 to the chromatograph subsystem 22 for analysis.

The sampling subsystem 26 forwards the fuel gas samples to the chromatograph subsystem 22, which separates the gas sample into its constituent parts and performs a quantitative analysis of each constituent. Gas chromatographs, such as utilized here, are well known tools to those skilled in the art. In the present invention, the remote analyzer module 20 which contains the gas chromatograph 22, provides not only a quantitative analysis, but presents the results of the analysis in a form suitable for processing in the remainder of the energy measurement system 11.

The actual informational output of the chromatograph subsystem 22 consists of a time varying signal as represented in FIG. 5, which varies over time in accordance with the qualitative and quantitative properties of the fuel gas being sampled. The intelligence contained in continuous waveform 500 consists of up to 15 gas constituents or components including non-combustibles, saturated and non-saturated hydrocarbons. Each constituent in the gas mixture under test is represented by a different peak in the time varying signal in FIG. 5 shown at 510 and 520, for example. This information is transmitted to the gas chromatograph interface 24 for further processing and conversion. The electronics in the interface subsystem 24 include a programmable gain amplifier system 75, detailed in FIGS. 4A-B, which is used to further process the analytical information supplied to it from the chromatograph subsystem 22.

Figure 4B:
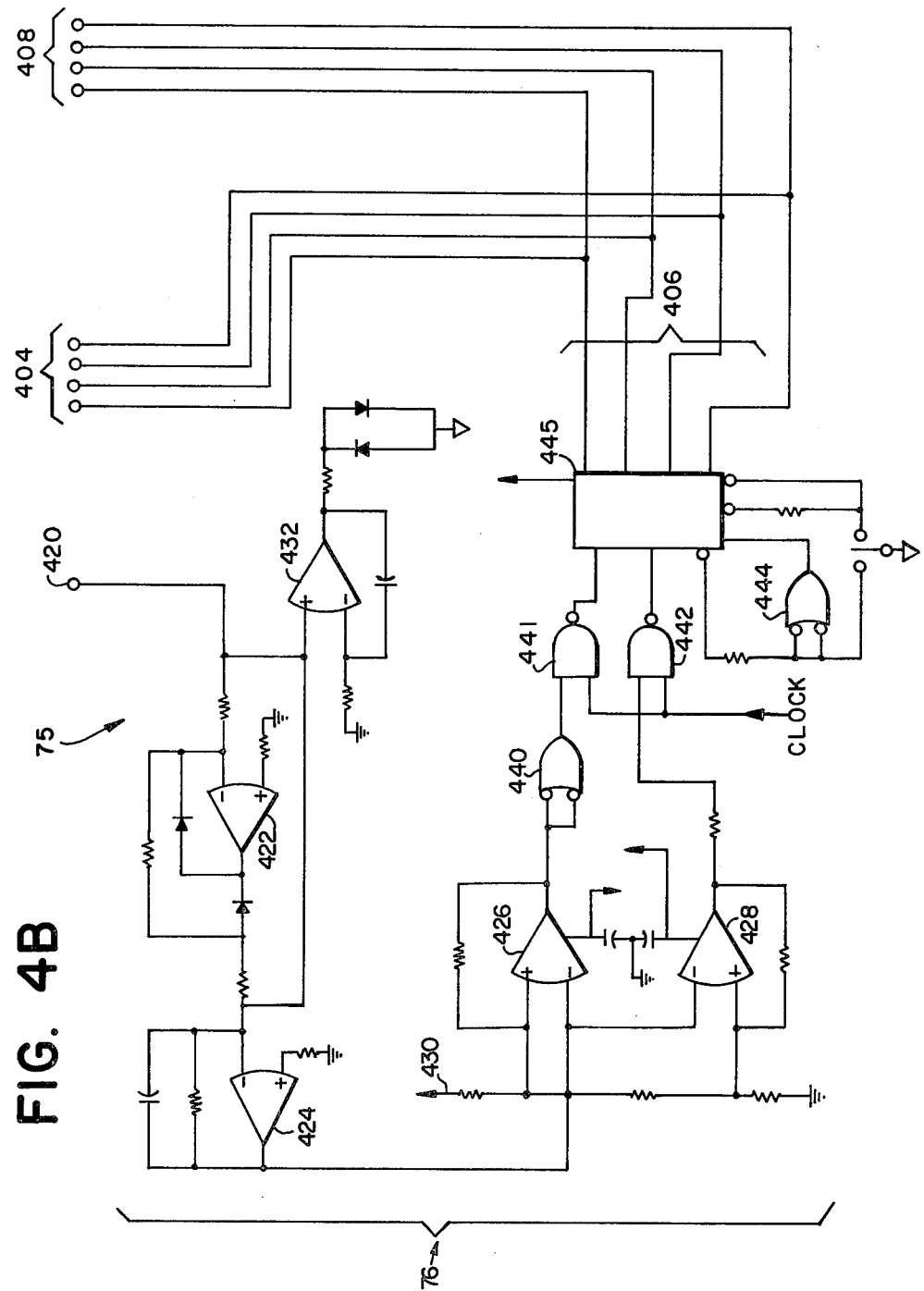

In FIG. 2, the programmable gain amplifier 75, is shown as comprising several components 72, 76, 78. FIGS. 4A-B further details, within the interface subsystem 24, the specific electronic circuitry utilized within amplifier system 75. System 75 utilizes a unique feedback technique for automatic gain control. The time varying signals produced by the chromatograph subsystem 22 are applied to the interface subsystem 24. These time varying signals are amplified after being conditioned by a filter 74, and then applied to analog/digital converter 78. As shown in FIG. 2 and detailed in FIGS. 4A-B the output of variable gain amplifier 72 is fed back to its input by way of a comparative circuit 76. This comparative circuit then programs the gain in the amplifier 72 such that its output level appears between 30% and 60% of the maximum amplitude allowable for converter 78. For example, if the output of the variable gain amplifier rises over 60% of the allowable maximum, the comparative circuit 76, sensing this, will lower the gain of amplifier 72. In a similar fashion, should the output of the variable gain amplifier go below 30% of the allowable maximum amplitude (for a given input signal), the comparative circuit 76 will sense this and raise the gain in the amplifier. The designed effect is to keep the output level of the variable gain amplifier within a fixed operating range.

In the preferred embodiment, the output of the variable gain amplifier is controlled within sixteen selectable gain ranges. As described, these gain ranges for amplifier 72 are controlled by the comparative circuit 76. The output from the variable gain amplifier 72 is fed to an analog to digital converter 78, as shown in FIG. 2, which reads the value of that output and converts it from analog to digital form consisting of twelve bits of digital information. In a similar fashion the gain setting of the variable gain amplifier 72, at one particular range, is represented by four digital bits. The gain setting determined by comparative circuit 76 is forwarded to the data bus 79. There it is combined with the analytical information from the output of amplifier 72, provided in digital form by analog to digital converter 78. Both the analytical information supplied by the chromatograph subsystem to amplifier 72, plus the gain setting of the variable gain amplifier 72, now in parallel digital form, flow to a conventional universal asynchronous receiver/transmitter (UART) 82 which allows the digital information compiled, in a parallel data format, to be transmitted serially over a common communications line such as a simple telephone cable. In the preferred embodiment, an information transmission rate of 9600 BAUD is used.

Transmission of this information from interface module 24 to control module 10 is accomplished through optical isolators used in conjunction with differential receivers 83 and 120, both being connected by communication line 14b. Use of optical isolators and differential receivers at both ends of line 14b eliminates noise within line 14b.

Another major component in system 11 consists of transducer interface module 30 shown in FIG. 1 and further shown in FIG. 2. Transducer interface module 30 processes data on certain parameters which are desired from the gas line 32 which are obtained from transducers in module 16. The apparatus utilized within module 16 measures static pressure, differential pressure, and temperature.

Transducer interface module 30 contains multiplexer 88, analog to digital converter 92, valve switcher 96 and universal asynchronous receiver transmitter (UART) 94. Multiplexer 88 samples information from line 13a which is connected to the transducers 104a-f, 106a-f and 102 as shown in FIG. 2. Multiplexer 88 selects each transducer under control of module 10, then forwards the sampled values to A/D converter 92. Converter 92 is connected to UART 94 which communicates in two directions with control module 10 through line 14a. Specifically, UART 94 receives signals from module 10 on which transducer multiplexer 88 should select. UART 94 also provides communications from module 10 in the form of instructions from computer 126 which control valve switcher 96. Switcher 96 is connected to motorized valves 108a through 108f in module 16, via line 13b. Switcher 96 comprises digital logic which upon receiving commands from module 10, opens a selected valve 108a–108f.

Turning to module 16 in FIG. 2, there is shown each of six metering tubes 116a–116f. The flow from the gas fuel pipeline 32 is directed into the module inlet 112 where it has access to the input of all six tubes. The gas flows through selected tubes in accordance with the selection of valves 108a–108f, and then returns to the pipeline 32 by way of outlet 114. The tubes 116 contain measurement orifices commonly used in the art for measuring flow. Six such measurement tubes are utilized in parallel. To allow for a large dynamic range of flow rates within the gas fuel line 32, each one of these six measurement tubes are of different size and diameter as to allow for operation within a particular range of flow rates. The tubes range in size from a very small diameter 116F corresponding to a small flow rate to a large diameter 116A for measurement of a large flow rate.

Each of the tubes 116a–116f have transducers to measure static pressure 104 and differential pressure 106. There is common temperature transducer 110 for the entire module 16. Lines 13a operatively connect these transducers with the multiplexer 88. Similarly, the motorized valves 108a–f at the exit end of each tube are connected by way of lines 13b, to tube switcher 96.

Tube switcher 96 opens or closes a selected motorized valve 108a–108f upon command from the control module 10. Control module 10 selects a tube or set of tubes on the basis of which tubes are operating within a range which will provide adequate resolution from the transducers in each tube. The result of utilizing six tubes in module 16 is that a large range of flow rates within pipeline 32 can be accommodated. The correct valves, and hence, the correct tubes are selected after a given flow rate is sampled through the tubes. This process is performed automatically and the flow data measured by each tube is sent, via interface module 30, back to the control module 10.

In addition to the physical parameters obtained by the transducer interface module 30 and the remote analyzer module 20, a communications module 40, shown in FIG. 1 is used to enter other constant parameters which may be entered into the system via a human operator. The communications module in the preferred embodiment consists of a hand held device containing a calculator keyboard 43 plus an alphanumeric readout 45 integrated into one portable unit 40. This communications module is used, among other things, to enter parameters such as orifice diameter and geometry, tube internal diameter, contract pressure, contract temperature, thermal expansion coefficients nd other nonvariable information. The basic control module 10 shown in FIG. 1 and further detailed in FIG. 2, performs the basic processing required to obtain the resultant information desired for energy measurement system 11. Module 10 contains a microprocessor, a strip printer 44, and various other control switches and indicators 46.

Figure 3:
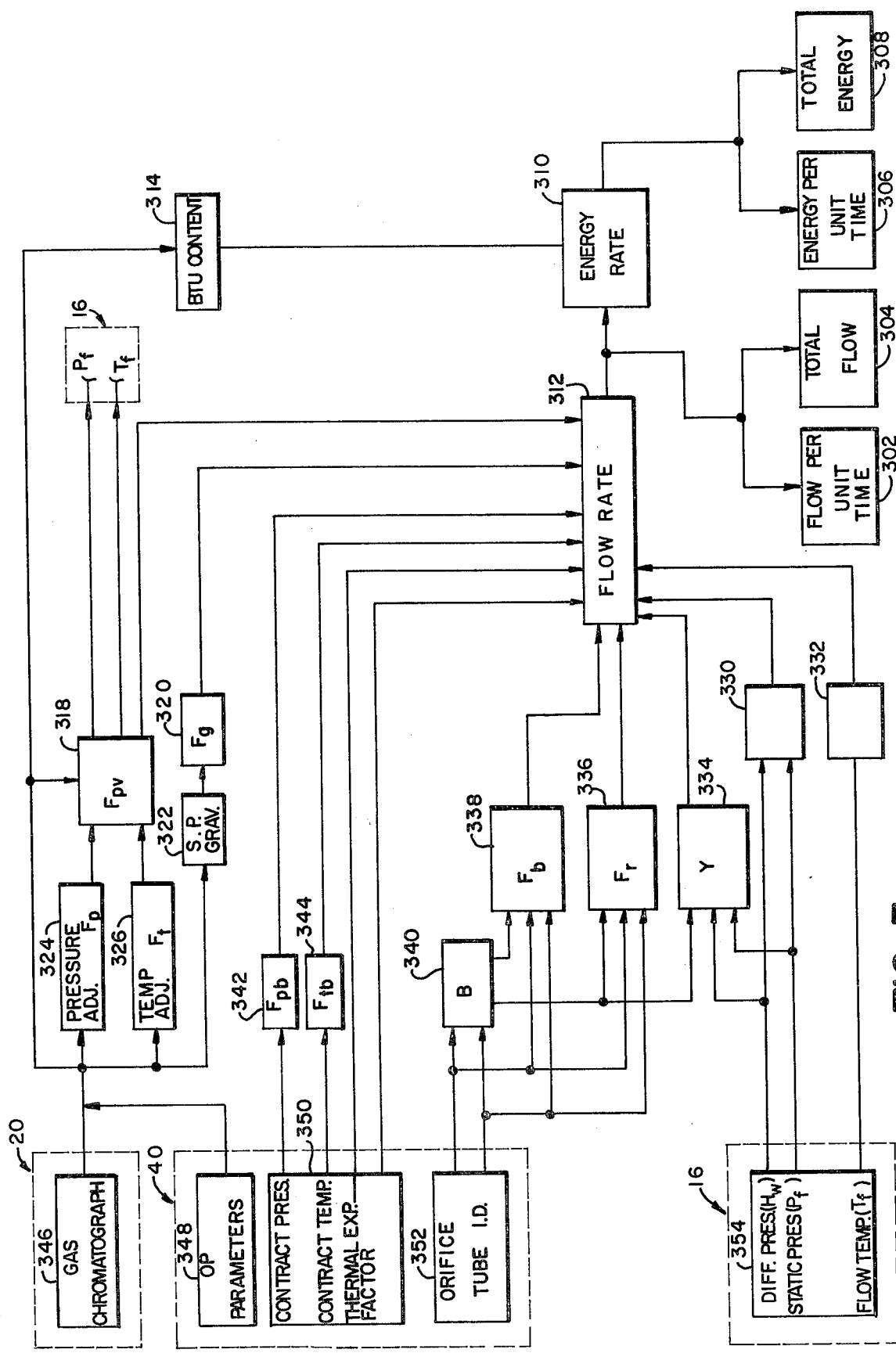
FIG. 3 is a functional block diagram of the energy measurement system of FIG. 1.

A computer program operating in conjunction with the computer, processes and analyzes the information applied to module 10 by both the remote analyzer module 20 and the transducer interface module 30. The information processing is shown in FIG. 3 and is described later.

Module 10 also controls the periodic sampling of fuel by the subsystem 26. Module 10 sends command signals through line 14b to UART 82 which transmits the command to subsystem 26 through line 125. These commands for example, in ten minute intervals, control the opening of the sampling tap 28 to obtain gas from pipeline 32 for testing. In addition, similar commands during calibration are used to select calibration gas 34, FIG. 1.

Module 10 integrates and analyzes the total of information provided into it by the various modules mentioned above. The outputs it obtains include gas volume flow for a given time period in addition to total flow overall. Additionally, total energy flow for a given time period is calculated as well as total energy overall. Other intermediate calculations for the final output are also available. This includes instantaneous flow rate, supercompressibility, BTU content and other intermediate results.

The basic control module 10 also provides analog signal outputs 52. These signal outputs 52 represent the information processed by the basic central module 10 which are displayed via digital readout 62, data strip printer 44 or the status panel 46 with its various indicator lamps. This information is forwarded to output 42 should it be desired to transmit the data over a remote telemetry system 50, or record the data over a long term utilizing a data recorder 60 such as shown in FIG. 1.

Turning now to FIG. 3, the information processing by BCM 10 will now be further described. Except for the insertion of the various input parameters, all of the information processing occurs within the basic control module 10, and its microprocessor 126 operates in conjunction with a computer program. The machine code for a typical gas mixture program is enclosed. The code presented is in hexadecimal format.

The operator parameters are entered via the communications module 40 described earlier. These parameters include constants such as contract pressure, contract temperature and thermal expansion factor. Also, the operator enters the geometry of the various tubes 116a–f within the flow transducer module 16. These constants include orifice diameters (d) and the inner diameters of each tube. Other system inputs include the gas chromatograph analysis supplied by module 20, and the temperature and static and differential pressure within each measurement tube in module 16.

The energy measurement system 11 uses certain analytical equations in its computations. These equations are used to compute energy content (BTU) 314, instantaneous flow rate 312, total energy 308 and total flow 304 as well as other intermediate results. Appended to this description is a list of equations used to obtain certain factors illustrated in FIG. 3. Also, the source of these equations are listed where appropriate. These equations are well known and may be found in American Gas Association publications. These publications include AGA-3, Gas Measurement committee Report #3, Orifice Metering of Natural Gas; AGA-5, Transmission Measurement Committee Report #5, Fuel Gas Metering; and NX-19, PAR Research Project NX-19, Manual for the Determination of Supercompressibility Factors for Natural Gas.

A complete compositional analysis of the gas sample is provided by analysis of the gas chromatograph module 20. Pressure adjustment factors 324 and temperature adjustment factor 326 are processed with the results of the chromatograph 346 from the chromatograph module 20. The adjustment factors 324 and 326 are forwarded, along with the chromatograph information 346, the static pressure and flow temperature from the flow transducer module 16, to calculate the supercompressibility factor Fpv at 318. The chromatograph information 346 is also forwarded to a BTU content calculation at 314. Additionally, chromatograph information 346 is directed to specific gravity calculation 322 which, in turn, is used to obtain a specific gravity factor 320.

The operator entered constants 350, entered through communications module 40, include contract pressure, contract temperature, thermal expansion factor $Fa_1$. The contract pressure is used to determine the pressure base factor 342. In a similar fashion, contract temperature is used to determine the temperature base factor 344.

The operator entered geometry 352 is entered via communications module 40. These entries consist of the orifice diameters and the inner diameters of the measurement tubes in module 16. These entries are used to determine a measurement factor B at 340. Also, they are forwarded along with B at 340, to determine the basic orifice factor 338. As shown, the orifice diameter d, tube inner diameter D and B at 340 are used to determine the Reynolds number factor (FR) 336.

The differential pressure, static pressure, and B at 340 are combined to obtain the expansion factor Y at 334. The static and differential pressures are combined in the equation shown at 330. Finally, the flow temperature is forwarded to obtain the flowing temperature factor at 332.

All of the above mentioned intermediate results are directed and combined to obtain a true gas flow rate at 312, as shown in FIG. 3. By utilizing all of the factors shown, an actual flow rate is obtained without relying on any assumed variables.

The BTU content 314, and the flow rate 312 are forwarded to determine the energy rate (in dekatherm) at 310. The flow rate 312 is used to determine the 24 hour accumulated flow 302 and the total accumulated flow 304. The energy rate 310 is utilized to determine the 24 hour total energy 306 and the overall total energy 308.

Returning now to the gas chromatograph interface subsystem 24, FIGS. 4A, 4B illustrate in detail the electronic circuitry utilized in the programmable gain amplifier 75.

The time varying signals from the chromatograph subsystem 22 enter circuit 75 at input 410, which is connected to the input of variable gain amplifier 72. Operational amplifiers 412 and 414, in conjunction with regulator 454 form a reference circuit also connected to amplifier 72 as shown. Amplifiers 412 and 414 operate in conjunction with their associated field effect transistors 490 and 492 to provide a constant current for a measurement thermistor within the chromatograph subsystem 22. Amplifier 412 provides a constant current through a reference thermistor (not shown) within subsystem 22 through line 411. In a similar manner, amplifier 414 provides a constant current through a measurement thermistor (not shown) within subsystem 22 through line 410. As the resistance of the thermistors changes due to the component composition of the gas, the voltage drop across each one varies. Accordingly, the voltage differential with respect to the two thermistors is applied to the input of amplifier 72.

Regulator 452 and operational amplifier 460 form a reference circuit utilized by analog to digital circuit 78. The output of amplifier 72 at line 420 contains the amplified signal which is applied both to A/D circuit 78 and to comparative circuit 76.

Circuit 76 comprises a plurality of operational amplifiers 422, 424, 426, 428 and 432. Amplifiers 422 and 424 together form a circuit providing an output polarity which is always positive irrespective of the polarity of the output of amplifier 72. Thus, amplifiers 422 and 424 transform the signal on line 420 to its absolute value without changing the signals informational content; either in frequency or amplitude. The output of amplifier 424 flows to the input of amplifiers 426 and 428. These two amplifiers compare the signal from amplifier 424 with a reference voltage at node 430. As described earlier, the purpose of comparative circuit 76 is to control the gain of amplifier 72 to keep its output within an optimum range for A/D circuit 78. By comparing the output signal of amplifier 424 with reference 430, amplifiers 426 and 428 provide three different states of operation. Should the output of amplifier 424 be very low, the voltages presented to amplifier 426 and 428 would cause their outputs to be high. A very high output of amplifier 424 would cause amplifiers 426 and 428 to produce a low output. The third condition would be present when the output of amplifier 424 is within an optimum amplitude. In this case, amplifier 426 would provide a high output while amplifier 428 presents a low output.

These various output conditions of amplifiers 426 and 428 then flow to inverter 440, and NAND gates 441, 442. These three elements operate such that clock pulses on line 475 will be applied to the appropriate control input of up-down counter 445 depending on the state of amplifiers 426 and 428. When the output of amplifier 424 is in the optimum range neither gate 441 or gate 442 will allow clock pulses at node 475 to flow to either the up or down count inputs of counter 445. Hence, the digital output value of counter 445 remains constant. Should both amplifiers 426 and 428 present high outputs to gates 440–442 only NAND gate 442 will allow clock pulses 475 to pass through. Since gate 442 is connected to the count down input terminal of counter 445, the counter will count down. Should both amplifiers 426 and 428 present a low output, NAND gate 441 would pass clock pulses 475. Gate 441 is connected to the up count input of counter 445 hence the counter would count up.

NOR gate 444 is used to counter 445 from over-counting or counting down when no signals are present from the output of amplifier 424. The switch associated with gate 444 is normally in the illustrated neutral position and is actuated for adjustment and alignment of circuit 75. Amplifier 432 functions to drive a pair of LED's which are used when the switch is actuated.

The output of up-down counter 445 comprises four bits of digital information in parallel which flow to output bus 406. Bus 406 is split to forward the output from 445 into two paths, bus 404 and 408. Bus 404 returns to the amplifier 72, thus completing a closed loop with the information on bus 404 being used to program the gain range of amplifier 72. Further, branch 408 of bus 406 applies the gain range information to bus 79 of circuit 78 and this information is forwarded to UART 82 for transmission to control module 10.

APPENDIX I
ANALYTICAL EQUATIONS

Total Flow rate ($Q_t$)

$$Q_t = \sum_{i=1}^{N} Q_i$$

where:
$Q_i$ = Instantaneous flow rate of ith tube
N = Total number of instrumented tubes Total Accumulated Flow (Q)

$$Q = \int_{t=0}^{t} Q_t \, dt \; (\text{ft}^3)$$

Total Energy Rate ($E_t$)

$$E_t = Q_t \times BTU$$

Total Accumulated Energy (E)

$$E = \int_{t=0}^{t} E_t \, dt / 10^6 \text{ Dekatherms}$$

Daily (24 Hour) Total Flow ($Q_{24}$)

$$Q_{24} = \int_{t=0}^{t=24} Q_t \, dt / 10^3$$

Daily (24 Hour) Total Energy ($E_{24}$)

$$E_{24} = \int_{t=0}^{t=24} E_t \, dt / 10^6 \text{ Dekatherms}$$

Energy Content (Dry Gross BTU)

$$BTU = \sum_{i=1}^{N} (Conc_i \times BTU_i)$$

where:
N = Number of detected components
$Conc_i$ = MOL% of ith component
$BTU_i$ = BTU content of pure component Specific Gravity (Composition)

$$SG = \sum_{i=1}^{N} (Conc_i * SG_i)$$

where:
$SG_i$ = Specific Gravity of pure component

Supercompressibility (Z)

$$1/Z = (0.99631) + 0.0101(SG) - 0.007 \; (NHC)$$

where: NHC = Σ Concentration of non-hydrocarbons

Real Gross Dry Energy Content $$RGDBTU = BTU/Z$$

Real Specific Gravity (RSG)

$$RSG = SG/Z$$

APPENDIX II
TABLE OF COMPONENTS

In measurement system 11, the following components have been used for the operation and function herein described.

| REFERENCE CHARACTER | COMPONENT | TYPE #/MFG. |
|---|---|---|
| 22, 26 | Gas Chromatograph and Manifold | 85.0002 Electronic Associates |
| 40 | Communication Module | HT-3 Termiflex |
| 72 | Programmable Gain Amplifier | 3606 Burr Brown |
| 82, 94, 124 | UART | CDP 1854 RCA |
| 88 | Multiplexer | DG506B Analog Devices |
| 78, 92 | A/D Converter | AD7550 Analog Devices |
| 96 | Time Switcher | MP240D2-4 Motorola |
| 126 | Digital Computer | Z80 Zilog |
| 445 | Counter | 40193 |
| 452, 454 | Reference Generator | MC1503A Motorola |

What is claimed is:

1. A system for measuring on line the total energy and total fluid flow of a gas mixture within a pipeline having widely varying component compositions and widely varying flow rates copmrising:

gas chromatograph means for producing time varying signals related to the component compositions of the gas mixture within the pipeline, programmable gain means coupled to said gas chromatograph means having a plurality of gain ranges, said programmable gain means having comparative means for selecting a gain range for optimum resolution and for producing a related gain range signal, means for converting to digital form the output of said programmable gain means, transducer means for measuring the pressure and temperature of said gas mixture within the pipeline, and control means coupled to said transducer means, said converting means and said gain range means for producing energy and flow rate signals of the gas mixture in the pipeline based on the on-line pressure, temperature, and component gas composition within a range related to the gain range signals.

2. The system of claim 1 in which said gas chromatograph means produces continuous time-varying output signals related to said component composition, said transducer means comprises first transducer means for measuring the temperature of the gas mixture in said pipeline, second transducer means for measuring the differential pressure of the gas mixture in said pipeline and third transducer means for measuring the static pressure of the gas mixture in said pipeline, additional means for converting to digital output form the measurements produced by said first, second and third transducer means, said control means includes first means for receiving said digital output from said additional converter means which is a function of the output of said second and third transducer means for producing total fluid flow rate signals, second means for receiving said digital output from said first named converter means which is a function of the output of said gas chromatograph means for producing energy content signals, third means for producing on-line total energy rate signals continuously in accordance with said energy content signals and fourth means for determining total accumulated energy of the gas mixture from the on-line determination of said total energy rate over a predetermined time period.

3. The system of claim 2 in which said control means includes means coupled to said converter means for correcting the total flow rate for deviation of the gas mixture being measured from ideal gas behavior by supercompressibility factor signals which are a function of the output of said first and third transducers.

4. The system of claim 3 in which there is provided first means for providing said factor to second means for compensating total flow rate signals in accordance with said temperature and pressure variations in said pipeline.

5. The system of claim 1 in which said programmable gain means includes amplifier means having said plurality of gain ranges, said comparative means being coupled between the input and output of said amplifier means for selecting one of said gain ranges for operating within the optimum resolution range of said converting means.

6. The system of claim 5 in which said comparative means includes means for providing a predetermined window of the resolution range of said converting means, means for (1) increasing the gain of said amplifier means when the time varying signal decreases in value below a lowest point of the window and (2) decreasing the gain of said amplifier means when the time varying signal increases in value above an upper point of the window.

7. The system of claim 6 in which said lowest point of the window is about 30% of the maximum amplitude of said converting means and in which said upper point of the window is about 60% of the maximum amplitude of said converting means.

8. The system of claim 1 in which there is provided transmitting and receiving means coupled between the control means and the converting means for sequentially transmitting the gain range signals in digital form to the control means.

9. The system of claims 1 or 8 in which there is provided a plurality of flow measurement tubes disposed in said pipeline for receiving the flow of said gas mixture, switcher means for selecting at least one tube through which the gas mixture is allowed to flow, said switcher means coupled to said control means for selecting particular tubes for producing optimum resolution of said measurements provided by said transducer means.

10. The system of claim 9 in which said transducer means includes first transducer means for measuring the temperature in the pipeline and second transducer means for each tube to measure the differential and static pressure within the respective tubes.

11. The system of claim 10 in which there if provided additional means for converting to digital form said temperature and pressure measurements of said first and second transducer means respectively, and said control means including means for receiving said digital signals from said additional converting means for noise free digital transmission to said control means.

12. The system of claims 1 or 8 in which said control means includes means for correcting the energy and flow rate signals by supercompressibility factor signals which are a function of gas pressure, temperature and component composition.

13. The system of claim 12 in which there is provided first means for determining the supercompressibility factor signals on line with variations in the gas pressure, temperature and component composition, and second means for determining flow rate signals accurately with the supercompressibility factor signals and in accordance with variations in gas pressure, temperature and component composition.

14. The system of claim 13 in which said control means includes third means for determining BTU content signals of the gas mixture in accordance with variations in component composition and fourth means for determining on line energy rate signals continuously in accordance with the BTU content signals.

* * * * *